United States Patent [19]
Hermann et al.

[11] Patent Number: 5,483,078
[45] Date of Patent: Jan. 9, 1996

[54] INK PENETROMETER HAVING FIBER OPTIC CABLES AND STATIONARY INK PADDLE

[75] Inventors: Raymond A. Hermann, Stamford; Peter L. Fagan, Redding, both of Conn.

[73] Assignee: Cytec Technology Corp., Wilmington, Del.

[21] Appl. No.: 227,848

[22] Filed: Apr. 14, 1994

[51] Int. Cl.⁶ ................................................. G01N 21/86
[52] U.S. Cl. ........................................ 250/559.32; 73/38
[58] Field of Search ................................. 250/571, 572, 250/559, 559.32, 559.27; 73/73, 38, 76, 159, 37, 84; 324/637, 646, 323, 468; 424/409, 427, 430, 436; 252/121, 122, 134; 356/382, 440

[56] References Cited

U.S. PATENT DOCUMENTS

| | | | |
|---|---|---|---|
| 3,150,264 | 9/1964 | Ehlert . | |
| 3,512,003 | 5/1970 | Berry et al. | 250/252 |
| 3,546,928 | 12/1970 | Ivarsson | 73/73 |
| 3,572,090 | 3/1971 | Graham et al. . | |
| 3,713,966 | 1/1973 | Lippke | 73/73 |
| 4,259,862 | 4/1981 | Sheaks et al. | 73/73 |
| 4,484,133 | 11/1984 | Riggin | 324/637 |
| 4,721,901 | 1/1988 | Ashley | 324/646 |
| 4,789,820 | 12/1988 | Parrent, Jr. et al. | 73/73 |
| 4,825,073 | 4/1989 | Smith, Jr. et al. | 250/260 |
| 4,927,496 | 5/1990 | Walkden | 162/136 |
| 4,976,138 | 12/1990 | Benninghoff et al. | 73/73 |
| 4,976,861 | 12/1990 | Pall | 73/73 |
| 5,138,870 | 8/1992 | Lyssy | 73/38 |

FOREIGN PATENT DOCUMENTS 03238345  10/1991  Japan .

OTHER PUBLICATIONS

A Liquid Penetration Test for Measuring the Sizing of Paper, Donna Price, R. H. Osborn, and J. W. Davis, Tappi, vol. 36, No. 1 pp. 42–46, Jan. 1953.

"Evaluation of the Hercules Sizing Tester," *Tappi Joint Papermakers/Testing Conf.*, 131–6, Sep. 25–27, 1973.

"Size Test for Paper Ink Resistance" (Hercules Method), *Tappi* T 530 pm–89, pp. 1–5 Jan. 1989.

*Primary Examiner*—Edward P. Westin
*Assistant Examiner*—Que T. Le
*Attorney, Agent, or Firm*—Claire M. Schultz; Ward & Olivo

[57] ABSTRACT

An improved penetrometer includes a stationary ink delivery system and an improved photohead, which connects to a light source and a photodetector via two fiber optic cables. A solid state electronic circuit automatically controls the operation cycle of the penetrometer, with a single start button controlling all operations of the instrument. In particular, there is no need to reset the clock timer to zero or to adjust the 100% reflectance value prior to each test. A ratio meter displays the ratio of the current reflectance to the locked-in initial reflectance in real time as the test proceeds.

20 Claims, 12 Drawing Sheets

INK PENETROMETER HAVING FIBER OPTIC CABLES AND STATIONARY INK PADDLE

FIELD OF THE INVENTION

The present invention relates to devices for measuring the rate at which a liquid, such as ink, penetrates a sample of fibrous material, such as paper, and, more particularly, to such devices having means for illuminating said sample and means for measuring the light reflected off said sample, thereby detecting the rate of penetration of liquid through said sample.

BACKGROUND OF THE INVENTION

In the manufacture of paper products, it is desirable to accurately and reliably measure the rate at which liquid penetrates through a paper sample. Such measurements are generally made using a device called a "penetrometer," which typically operates by measuring the time needed for a colored 18 liquid (hereinafter referred to generically as "ink") to penetrate through a sample by monitoring the light reflectance of 20 the opposite side of the sample to detect appearance of the penetrated ink. U.S. Pat. No. 3,512,003, for example, discloses such a penetrometer. Another well known penetrometer is the Hercules Sizing Tester, as described in "Evaluation of the Hercules Sizing Tester," *TAPPI Joint Papermakers/Testing Conf.*, 131-6, Sep. 25–27, 1973.

Conventional ink penetrometers—such as the '003 device—deliver ink to the sample-under-test by means of a paddle or well which is raised by a pneumatic system so that the ink contacts the sample to begin the test. Unfortunately, this pneumatic system is difficult to calibrate and maintain, and yet its calibration and maintenance is critical to the accuracy of the penetrometer.

In view of the above, one object of the present invention is a highly accurate and reliable ink penetrometer.

Another object of the invention is a penetrometer with single push-button operation, including automatic sampling and lock-in of the 100% reflectance value of the sample prior to the test, automatic control of a run timer, single fill pump action, automatic drain and automatic status display.

Still another object of the invention is a penetrometer having reduced maintenance requirements.

Yet another object of the invention is a penetrometer in which fresh, uncontaminated ink is used for each test, and which requires only occasional cleaning of the ink paddle.

Another object of the invention is a penetrometer which utilizes modern, solid state control and measurement circuitry.

Still another object of the invention is a penetrometer having an improved ink delivery system.

Yet another object of the invention is a penetrometer having a compact photohead which employs modern, fiber optic technology.

Still another object of the invention is a penetrometer including means for outputting and/or displaying, in real time, the ratio of current reflectance to an initial, locked-in reflectance value as the testing cycle progresses.

Another object of the invention is a penetrometer in which the light source and detector are separated from each other, and both are separated from the chemical environment of the fluid, thereby increasing the stability and durability of the sensors.

SUMMARY OF THE INVENTION

The above, as well as other, objects and advantages are realized, in accordance with one aspect of the invention, by a penetrometer comprising: (1) means for applying fluid to a first surface of a sample; (2) means for optically detecting the penetration, or the extent of penetration, of said fluid to, or proximate to, a second surface of said sample; and (3) timing means, coupled to said means for applying and said means for optically detecting, for measuring the time required to penetrate, or to reach a predetermined degree of penetration, of the fluid to or proximate to said second surface; wherein said means for applying fluid remains in a fixed position with respect to said sample. Alternatively, said timing means is coupled to said means for applying fluid and said means for optically detecting, and measures the time between the application of said fluid to said first surface and the optical detection of said fluid on or proximate to said second surface. The optical detection preferably operates by monitoring the light reflectance or absorption of said second surface.

In accordance with another aspect of the invention, a penetrometer for measuring the rate of penetration of a fluid into a sample comprises: (1) means for applying fluid to a first surface of said sample; (2) means for optically detecting the penetration of said fluid to a second surface of said sample comprising: (a) means for illuminating said second surface comprising a light source and a first fiber optic cable; and (b) means for detecting light reflected from said second surface comprising a second fiber optic cable and a photodetector; and (3) timing means, coupled to said means for applying and said means for optically detecting, for measuring the time between the application of said fluid to said first surface and the detection of a diminished level of light reflected from said second surface indicating that said fluid is on or proximate to said second surface. Advantageously, the invention may include two or more independently operating penetrometers (each having a photohead, ink paddle, etc.) mounted in the same cabinet, in which case the first fiber optic cables are preferably merged to form a single bifurcated fiber optic cable with its merged end attached to a single light source and each of its split ends attached to a different photohead. Use of fiber optic cables in the penetrometer offers several advantages: (1) more uniform illumination of the sample; (2) smaller photohead; (3) ability to minimize interference between source and photodetector, particularly thermal interference; and (4) isolation of the source and photodetector from the chemical environment of the sample and fluid.

BRIEF DESCRIPTION OF THE DRAWINGS

The present invention will be more fully understood with reference to the Detailed Description below, which is intended to be read in conjunction with the following set of drawings, in which.

DETAILED DESCRIPTION OF THE PREFERRED EMBODIMENT

Figure 1:
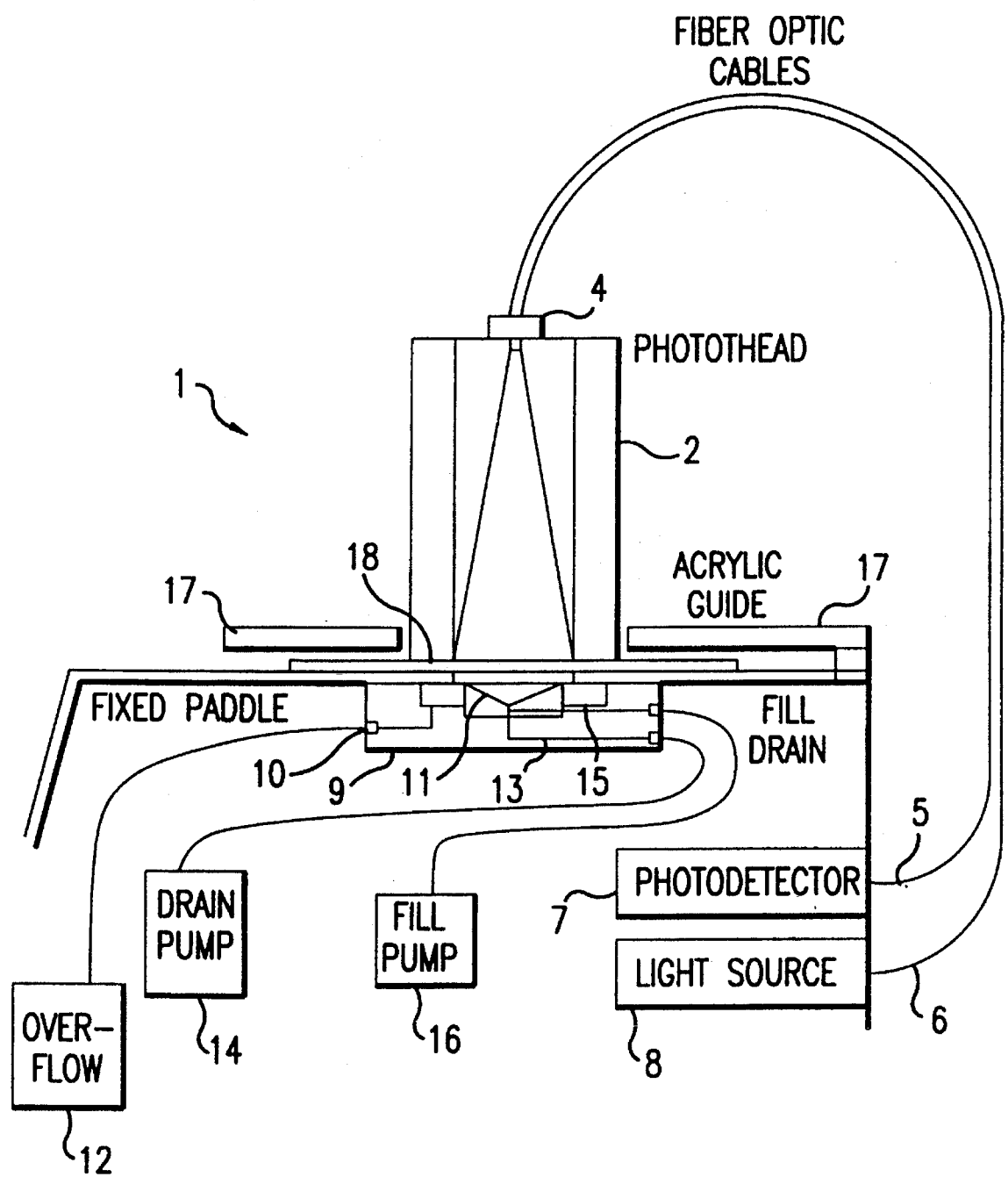
FIG. 1 depicts of the overall physical structure of a penetrometer 1 in accordance with the invention.

Reference is now made to FIG. 1, which depicts the overall physical structure of the penetrometer of the present invention. The ink delivery portion of penetrometer 1 includes a fixed ink paddle 9 having an ink well 11, a drain port 13 for removing ink from well 11, a (preferably angled) fill port 15 for injecting ink into well 11 and an overflow port 10 for collecting ink that overflows well 11. Penetrometer 1 initiates a test by directing fill pump 16 to pump a fixed quantity of ink into well 11 sufficient to cause ink to completely contact a first surface of sample 18. At the completion of a test, drain pump 14 removes the remaining ink from well 11 via drain port 13. Importantly, because of the preferably angled configuration of fill port 15 with respect to drain port 13, the ink removal process leaves fill port 15 filled with ink. Thus, there are no "air bubbles" and the like in fill port 15, which permits delivery of a much more precise and uniform spot of ink to the paper at the beginning of each test, thereby increasing the accuracy and reliability of the penetrometer.

Fill pump 16 is a synchronous drive pump, while drain pump 14 and is a solenoid driven piston pump. Overflowing fluid is gravity fed to a capture box 12, which contains any leaks in the tubes and fittings. Fill pump 16 is preferably a precision metering pump, which delivers a precise volume of liquid per unit time. Drain pump 14 should be self-priming and preferably capable of operating dry without damage.

Another part of penetrometer 1 that is visible in FIG. 1 is its means for optically detecting the penetration of ink to a second (top) surface of sample 18, which comprises: a photohead 2; a light source 8; a first fiber optic cable 6 for communicating light from source 8 to photohead 2; a photodetector 7; a second fiber optic cable 5 for communicating light from photohead 2 to photodetector 7; and a mounting 4 for affixing fiber optic cables 5 and 6 to photohead 2. Optionally, fiber optic cables 5 and 6 can be replaced by a single bifurcated fiber optic cable, with the merged end of the bifurcated cable connected to photohead 2. Photohead 2 is preferably made from a black, nylon material (available under the trademark DERLIN), which reduces light reflection by the internal surfaces. Light source 8 comprises a halogen lamp with a built-in lens, and is powered by the same D.C. power supply that powers the electronics (described below).

Photodetector 7 has associated therewith a built-in amplifier and is advantageously located away from the chemical environment of the ink well 11 and sample 18, to avoid deterioration caused by the ink and/or solvent vapors within photohead 2. Also, the stability of photodetector 7 is enhanced due to its increased separation from light source 8, as compared to prior art designs wherein both were integrated within photohead 2. In particular, photohead 2 eliminates problems of thermal drift, light bleedthrough and chemical exposure previously associated with photodetector 7.

Acrylic guides 17 position photohead 2 above fixed inkwell 11, with sample 18 being positioned anywhere between the two. The entire assembly of penetrometer 1 can be easily cleaned. Importantly, normal cleaning requires no disassembly. The inking paddle is cleaned simply by squirting clean water on the inkwell and running the drain pump in manual mode with a front panel switch.

Figure 2:
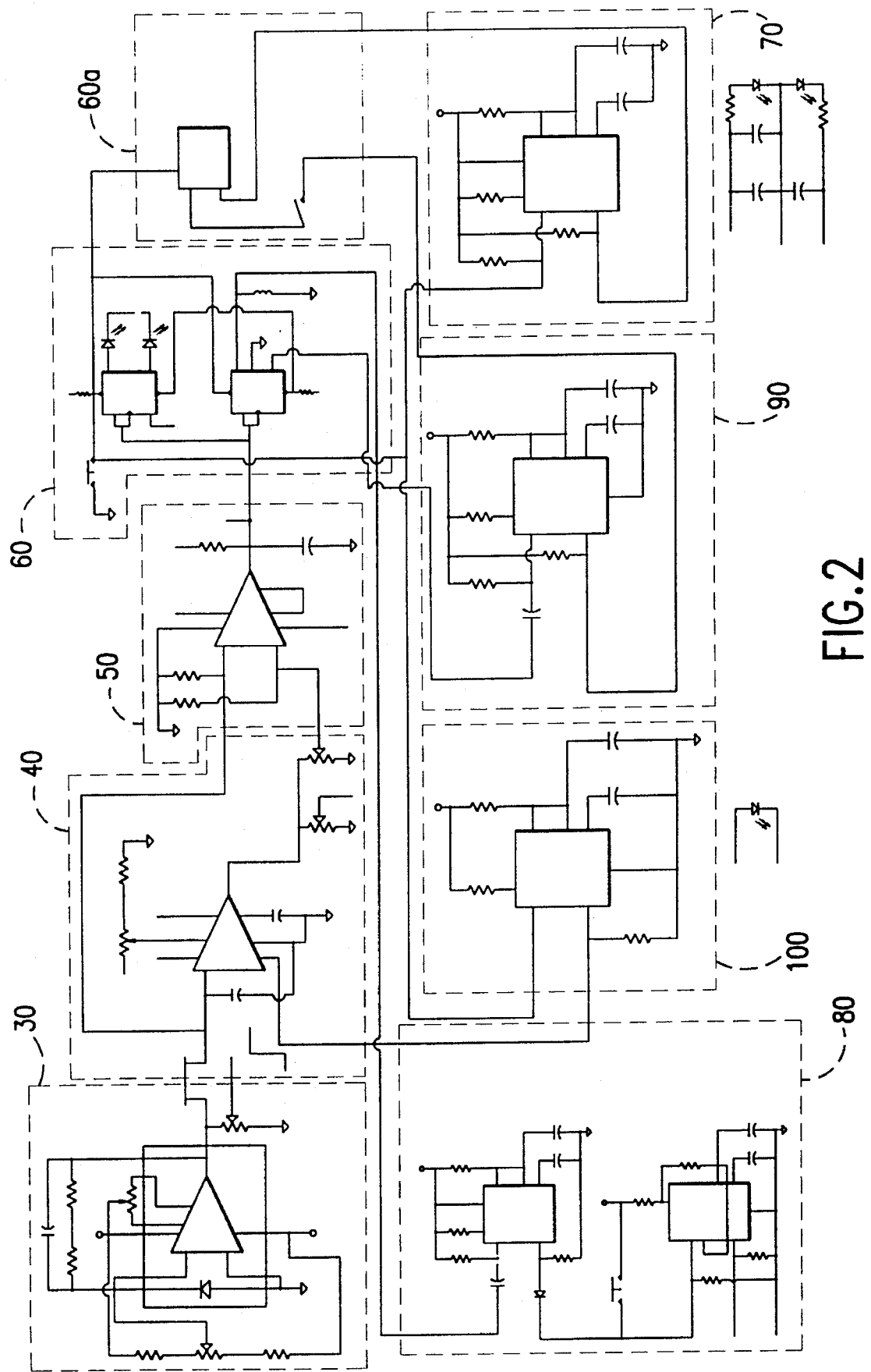
FIG. 2 depicts the various connections between functional components of the electronics of penetrometer 1.

FIG. 2 depicts the interconnections between the various electronic functional blocks in penetrometer 1, including: photodetector amplifier 30, sample & hold amplifier 40, voltage comparator 50, latched flip-flop 60, clock timer 60a, clock timer reset circuit 70, drain timer 80, fill timer 90, and sample & hold timer 100.

Figure 3:
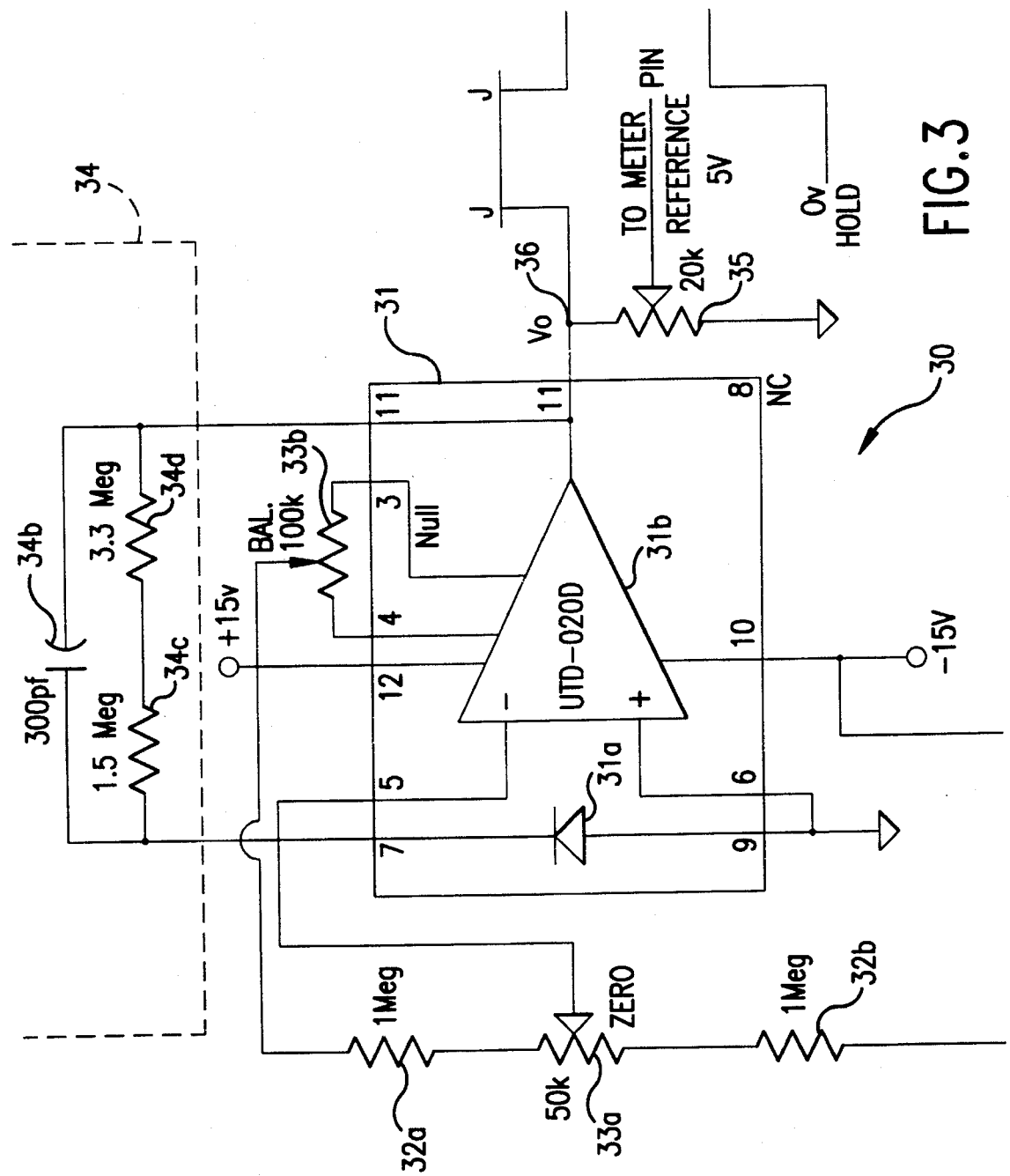
FIG. 3 is a schematic diagram of a photodetector amplifier 30 in penetrometer 1.

Referring now to FIG. 3, a photodetector amplifier 30 includes a UTD-020D integrated circuit 31, having a photodiode 31a and a built-in operational amplifier 31b integrated therein. Built-in amplifier 31b, in combination with feedback impedance 34 (which includes filter capacitor 34b and resistors 34c–d), is wired to amplify the signals generated by photodiode 31a. Resistors 32a–b and potentiometers 33a–b provide appropriate offset and zero adjustments. Voltage divider 35 is used to calibrate the range of a digital panel meter (not shown), which displays the ratio of current reflectance to initial, locked-in reflectance. Photodetector amplifier 30 provides an output signal on node 36.

Figure 4:
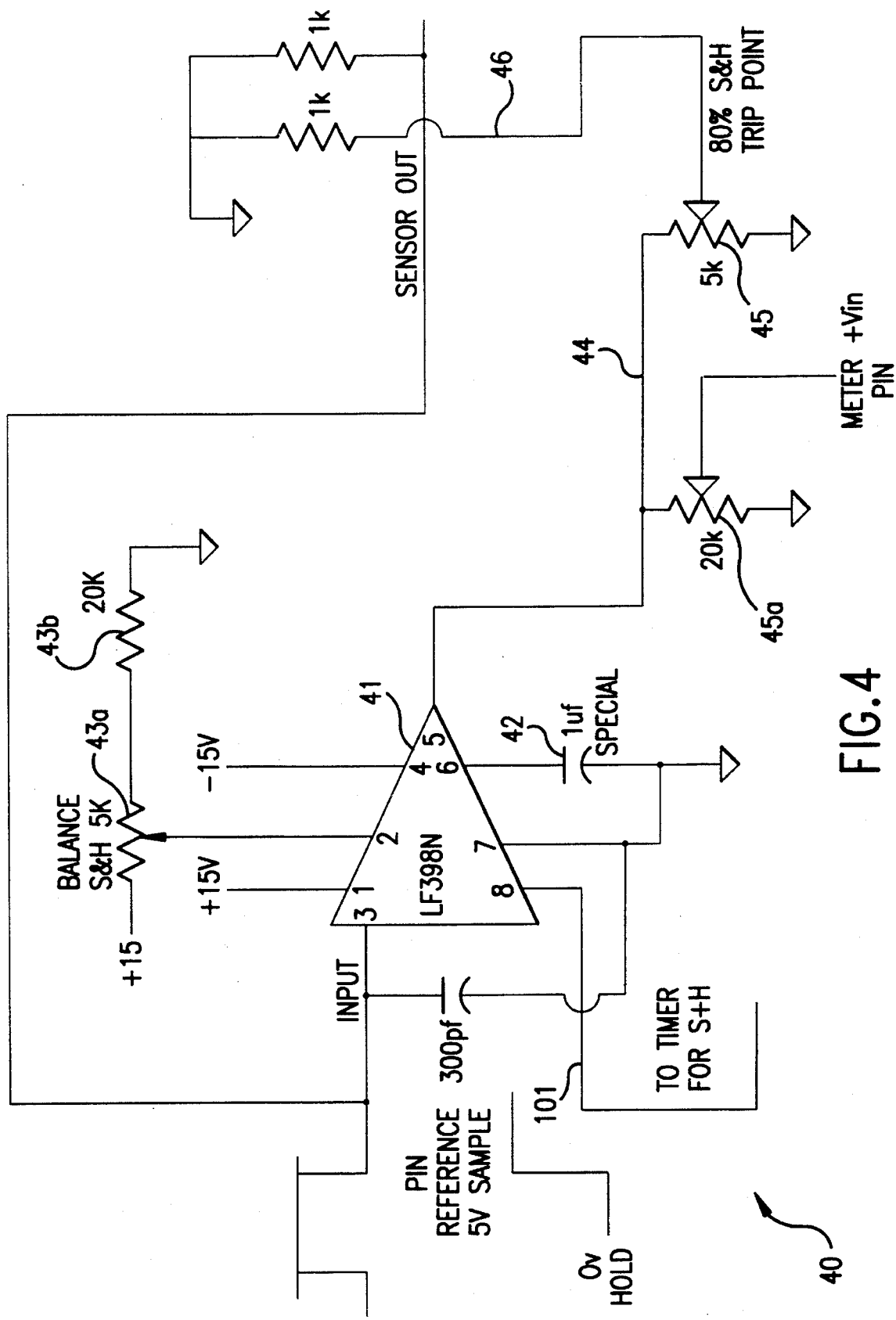
FIG. 4 is a schematic diagram of a sample & hold amplifier 40 in penetrometer 1.

Referring now to FIG. 4, sample & hold amplifier 40 includes an LF398N operational amplifier 41. Hold capacitor 42 is preferably a very low leakage capacitor and holds the voltage present on node 36 at the instant node 101 makes a high-to-low transition, assuming that said voltage has been stable for at least a minimum sampling time, which is set by sample & hold timer 100. Hold capacitor 42 and sample & hold amplifier 40 are preferably selected to achieve a minimum droop rate. Resistor 43b and potentiometer 43a provide offset calibration. Voltage divider 45 is preferably set to divide the sample & hold output voltage 44 to 80%, or any other predetermined percentage, of its final test point value at node 46. Voltage divider 45a sets the locked-in initial voltage value to the ratio meter. This value is then compared to the real time reflectance voltage from node 35 to develop a true ratio reading, which is displayed on a meter in real time.

Figure 5:
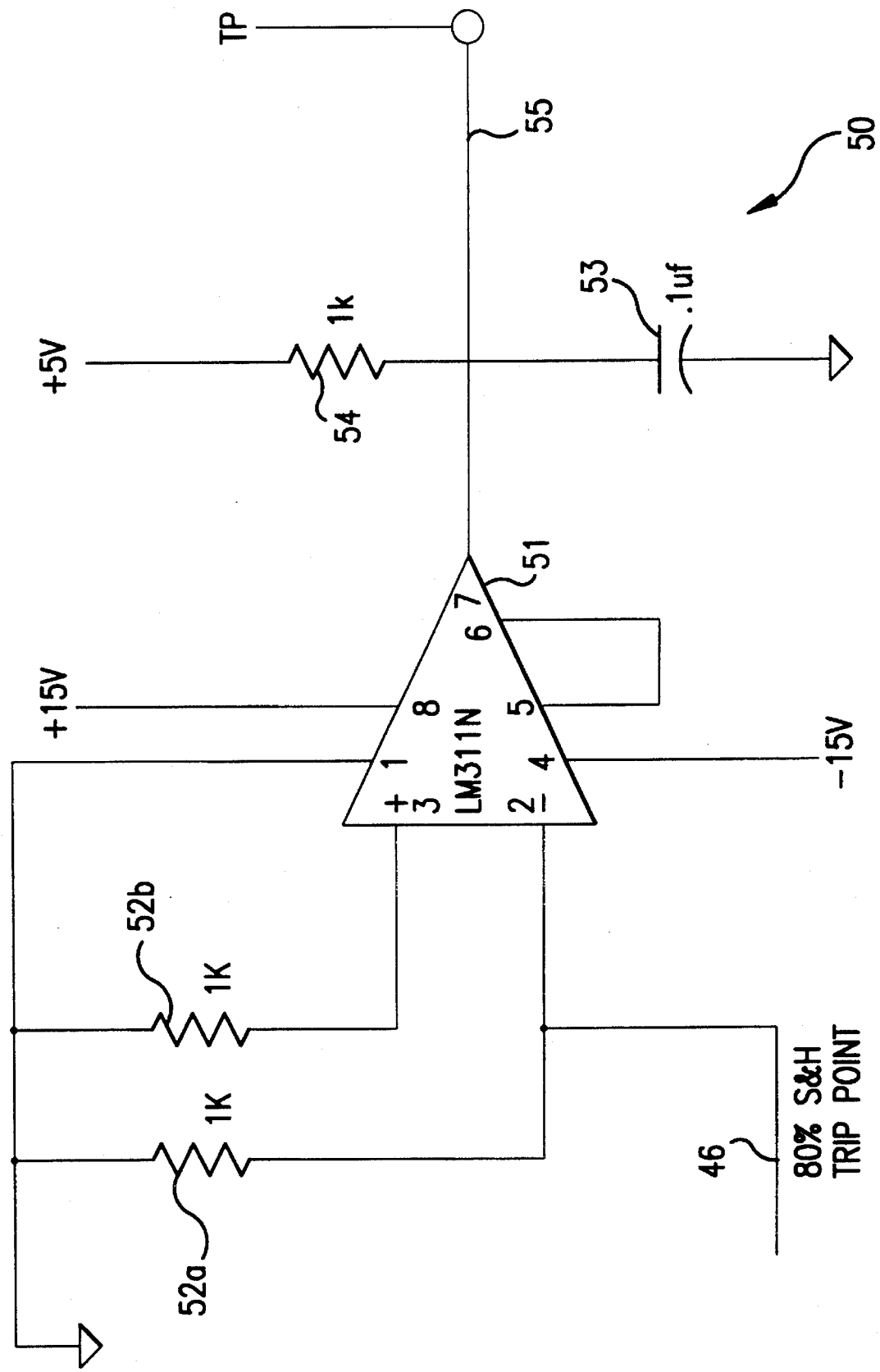
FIG. 5 is a schematic diagram of a voltage comparator 50 in penetrometer 1.

Referring now to FIG. 5, voltage comparator 50 includes an LM311N operational amplifier 51 wired to function as a comparator. Resistors 52a–b set the input impedance of comparator 50, and clamp the inputs to a reference low value. Resistor 54 and capacitor 53 determine the output waveform—i.e., value, rise time, fall time—at output node 55, which drives the latched flip-flops. Comparator 50 compares the present sensor amplifier output 36 to a held value 46 (which is preferably 80%, or any other predefined percentage, of the full reflectance output voltage at the start of the test—i.e., before any of the fluid has penetrated through the sample). Thus, comparator 50 triggers when the fluid that has penetrated the sample causes the reflectance off the second surface of the sample to drop preferably by 20%, or whatever predefined percentage has been set at voltage divider 45.

Figure 6:
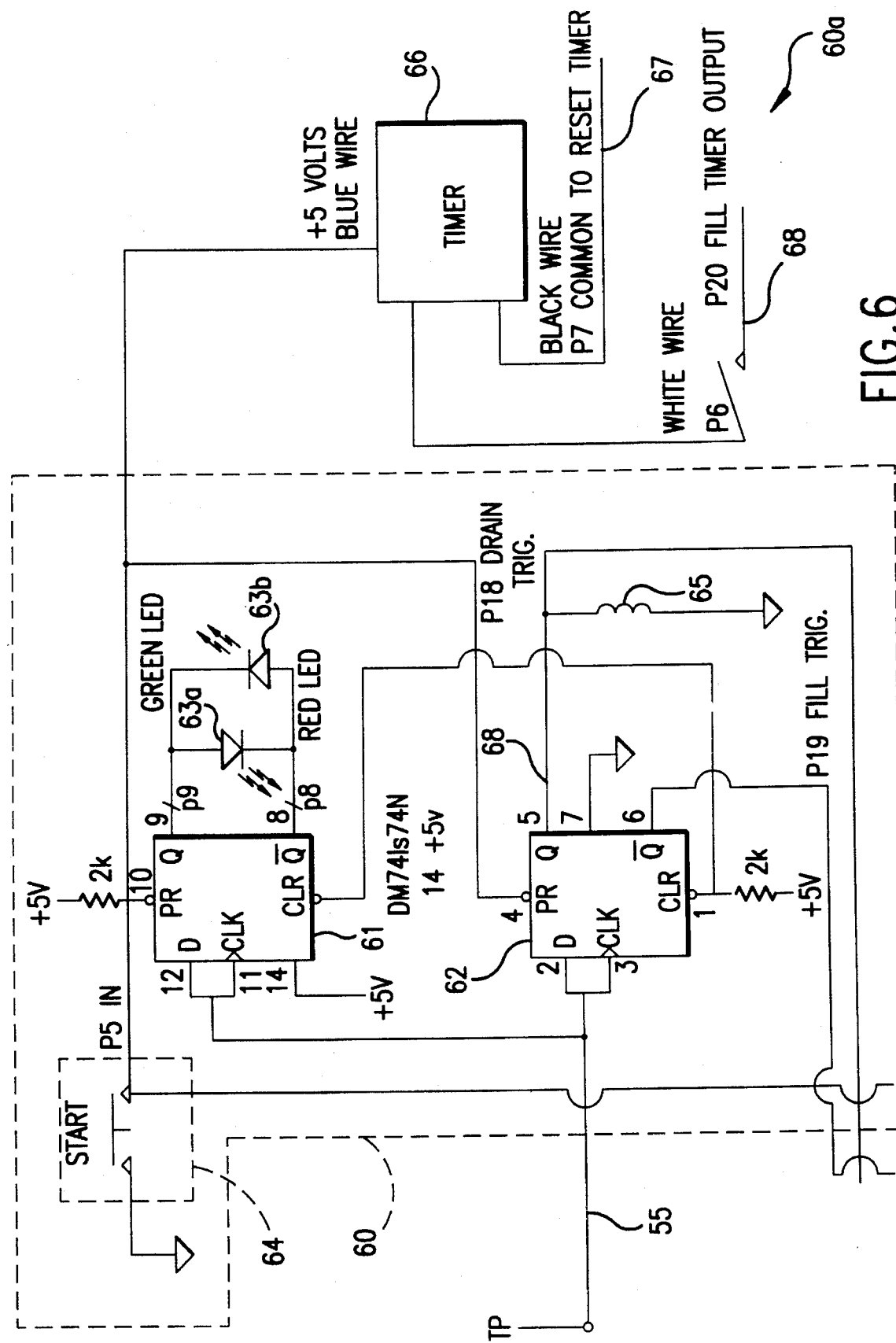
FIG. 6 is a schematic diagram of a latched flip-flop 60 and a clock timer 60a in penetrometer 1.

Referring now to FIG. 6, latched flip-flops 60 include D flip-flops 61 and 62. Q-output 268 of flip-flop 62 drives a Reed relay coil 65, which controls clock timer 60a, which resets at the beginning of each test and records the elapsed time for each test. Timer 66 includes a meter that displays the run time of test (in seconds) as it proceeds from the 100% reflectance 9 start point to the end point (preferably 80% reflectance). Timer 66 has three modes: (1) providing a running display of accumulated time while a test is in progress; (2) holding the display of total test after a test has completed; and (3) resetting to zero and holding until the fill pump action is complete and the test commences. The action of Reed relay 65 and latched flip-flop 62, triggered by a high signal from the fill timer output at node 268 (and also the reset timer), produce the three states for timer 66. Flip-flop 62 also provides a trigger pulse at node 269 to start the fill timer, which runs the fill pump. Using a latched signal ensures that the fill pump will run only once per test cycle, regardless of how many times a user pushes start button 64 during the test cycle. Flip-flop 61 drives LEDs 63a–b. which illuminate, respectively, to indicate test-in-progress or test-complete.

Figure 7:
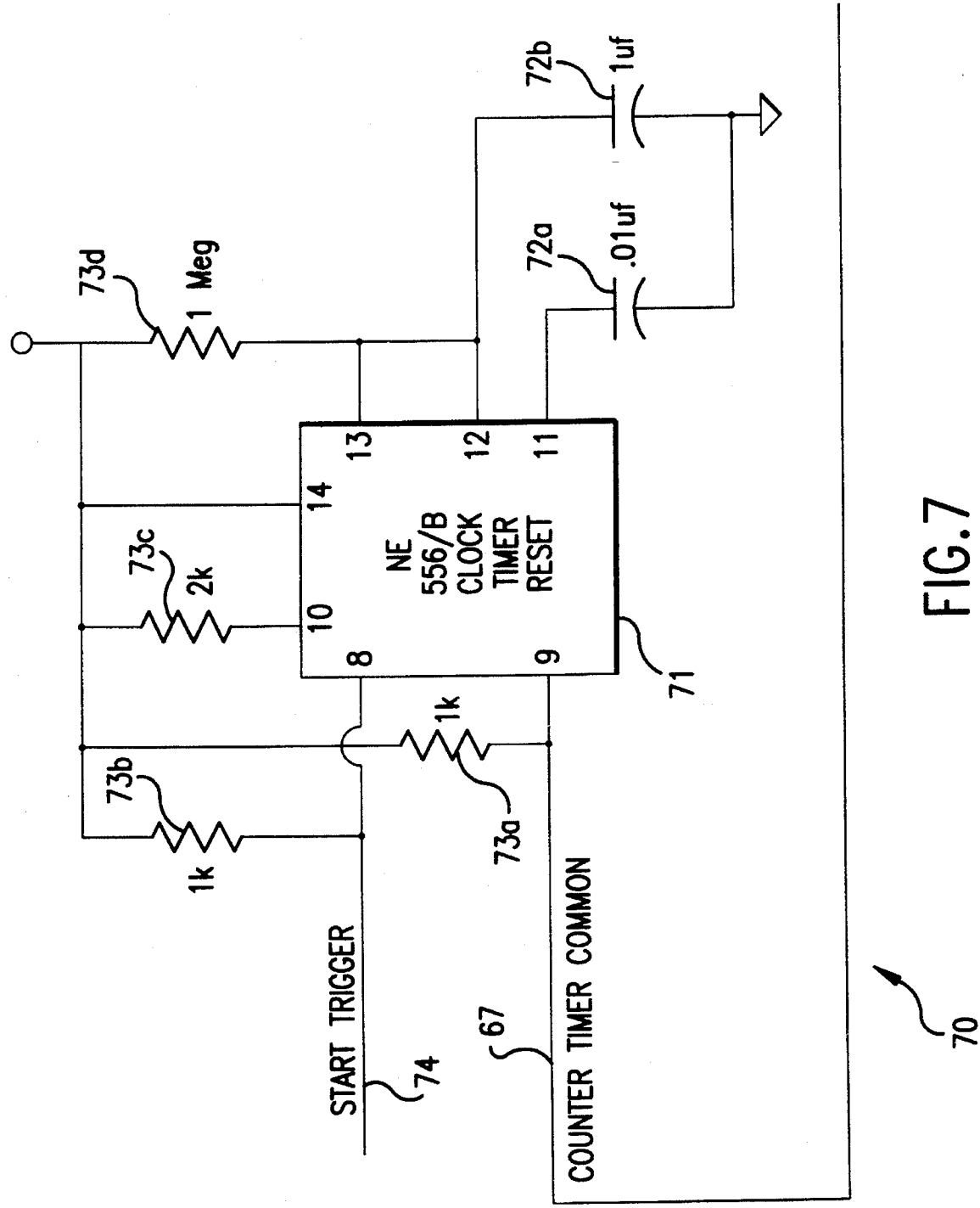
FIG. 7 is a schematic diagram of a clock timer reset circuit 70 in penetrometer 1.

Referring now to FIG. 7, clock timer reset circuit 70 includes one half of a 556/B integrated circuit 71, resistors 73a–d and capacitors 72a–b. Reset circuit 70 provides a pulse on line 67 that resets clock timer 60a to zero at the beginning of each test cycle.

Figure 8:
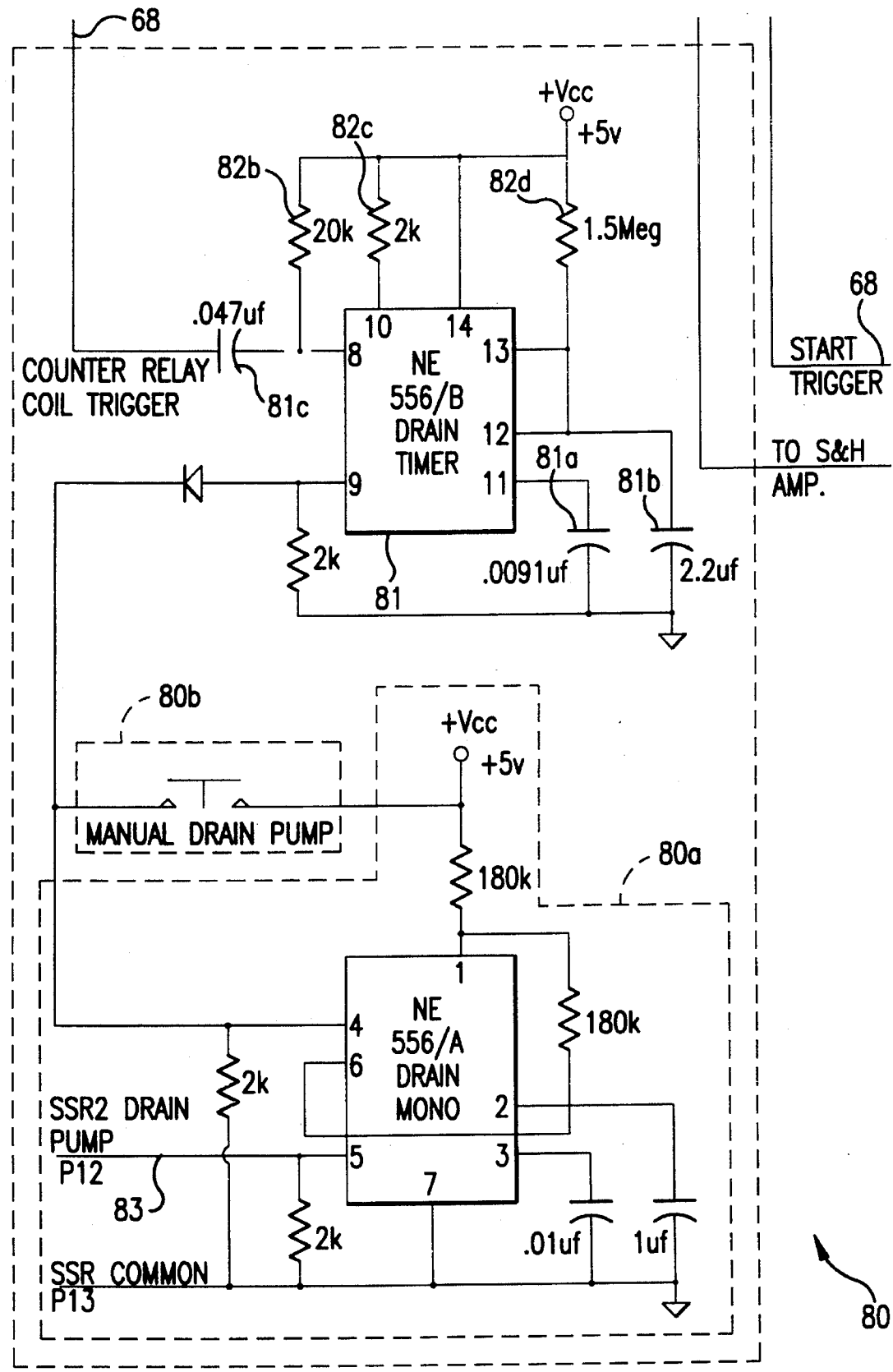
FIG. 8 is a schematic diagram of a drain timer 80 in penetrometer 1.

Referring now to FIG. 8, drain timer 80 includes a 556/B integrated circuit 81, resistors 82a–d and capacitors 81a–c, as well as a manual drain pump override circuit 80a, which is activated by a manual drain pump override switch 80b. Drain timer 80 provides a control signal on line 83 to operate drain pump 14 for a time period sufficient to drain all remaining ink from well 11 at the end of a test cycle. A trigger signal on line 268 (and generated by latched flip-flop 62) directs drain timer 80 to automatically run the drain pump at the end of each test.

Figure 9:
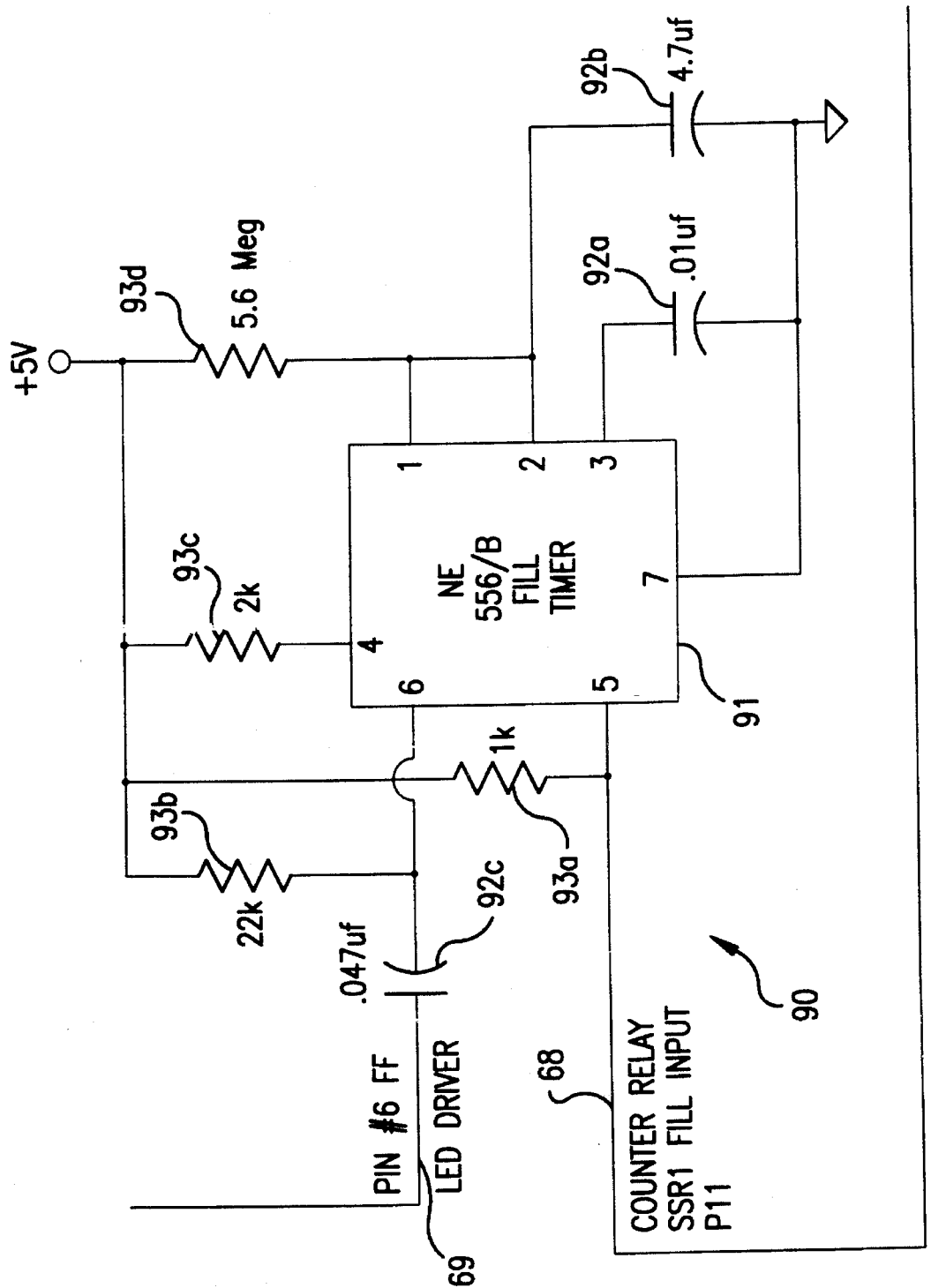
FIG. 9 is a schematic diagram of a fill timer 90 in penetrometer 1.

Referring now to FIG. 9, fill timer 90 includes a 556/B integrated circuit 91, capacitors 92a–c and resistors 93a–d. Fill timer 90 provides a control signal on line 168 to direct fill pump 16 to completely fill ink well 11 at the beginning of each test cycle. Capacitor 92c couples a change-of-state of latched flip-flop 62 to produce a single run of the fill pump, independent of any actuation of the start button, which eliminates overflow and flooding of the instrument.

Figure 10:
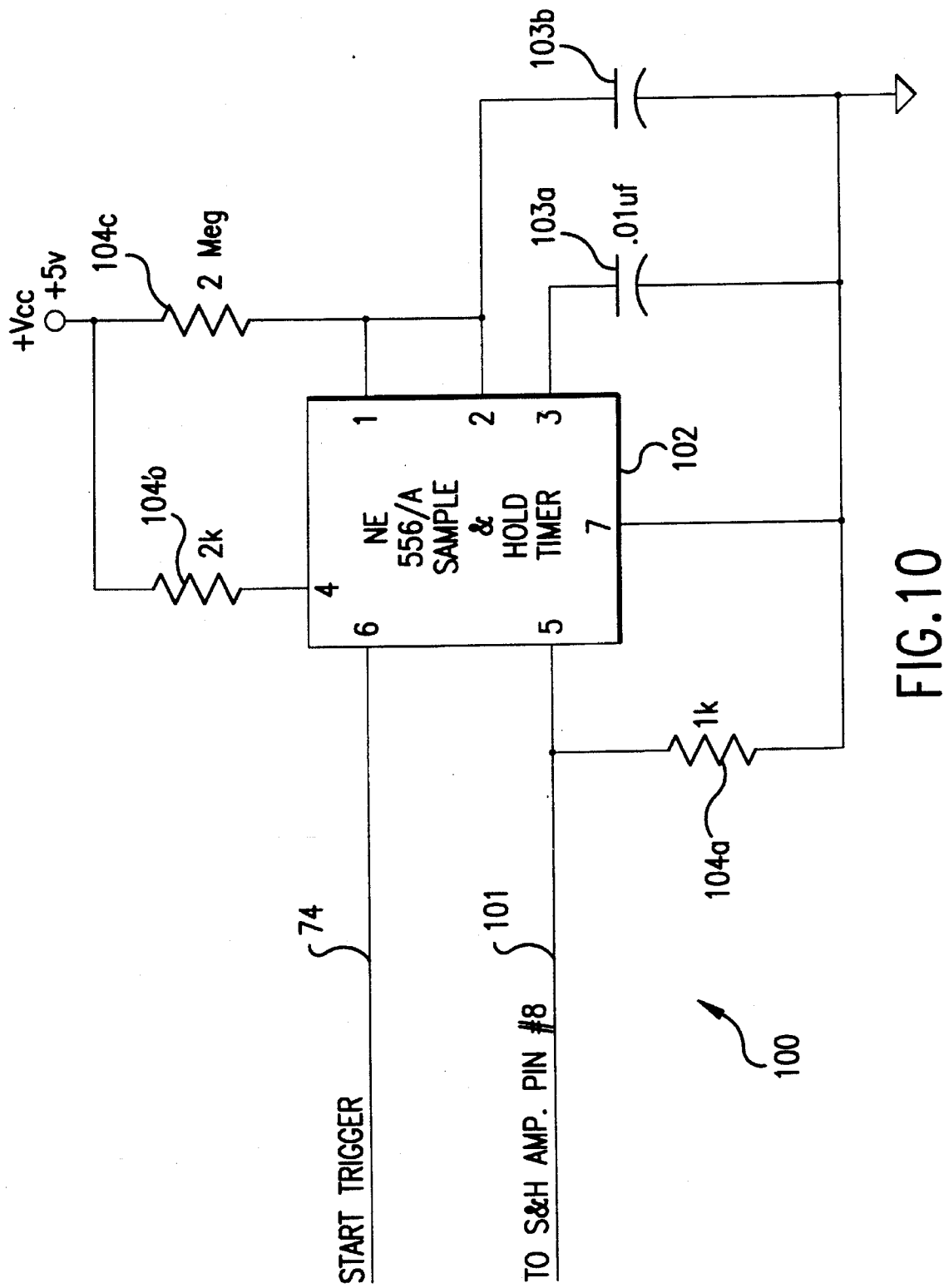
FIG. 10 is a schematic diagram of a sample & hold timer 100 in penetrometer 1.

Referring now to FIG. 10, sample & hold timer 100 includes a 556/A integrated circuit 102, capacitors 103a–b and resistors 104a–c. Sample & hold timer 100 generates a pulse on line 101 which causes sample & hold circuit 40 to lock-in and hold an initial reflectance value at the start of each test cycle. The shape of the leading edge of the pulse on node 101 is important to ensure correct action of the sample & hold amplifier.

TEST RESULTS: EXAMPLE 1

Four penetrometers in accordance with the present invention were used to measure the rate of penetration in paper and thereby provide paper sizing values. Two sets of internally sized paper, representative of typical office copier paper (70 g/m² basis weight with 12% calcium carbonate as filler), were selected. One set of paper had a relatively low sizing and the other set had a relatively high sizing. Eight sheets of paper from each set were tested on each of the four penetrometers of the present invention as well as on five other conventional penetrometers of the type previously used in the art.

The fluid used in the test was an ink composed of aqueous 1.25% Naphthol Green B dye buffered at PH 7. The sizing value was recorded as the times in seconds for the reflectance to drop to 80% of its original value, i.e. the original reflectance of the ink free paper surface opposite the surface initially exposed to the ink.

Figure 11:
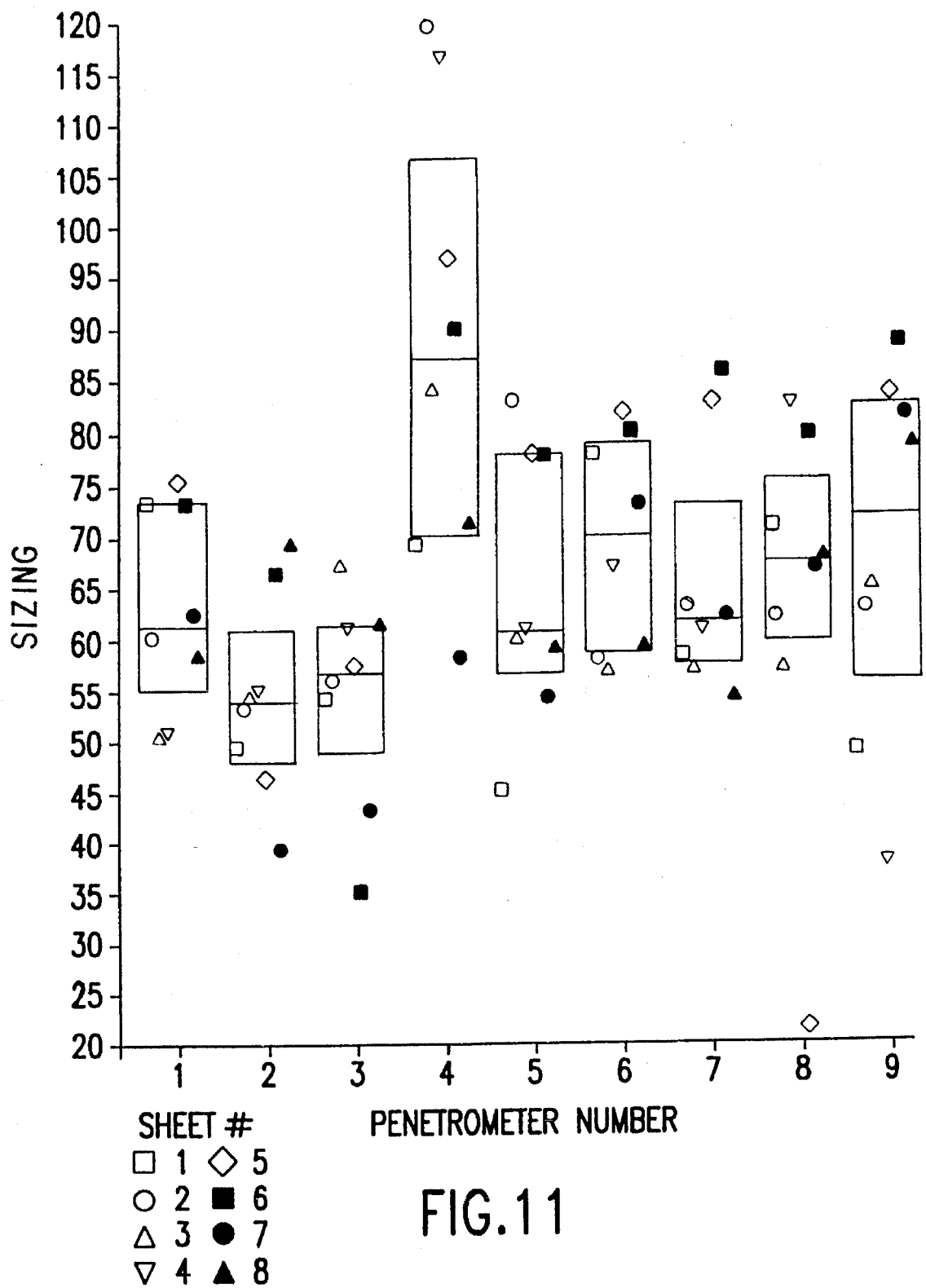
FIG. 11 is a plot of the data in Table 3 and depicts measurements of mean sizing value and IQR obtained by both conventional penetrometers and penetrometers according to the invention for eight sheets of low sizing paper; and, FIG. 12 is a plot of the data in Table 4 and depicts measurements of mean sizing value and IQR obtained by both conventional penetrometers and penetrometers according to the invention for eight sheets of high sizing paper.
Figure 12:
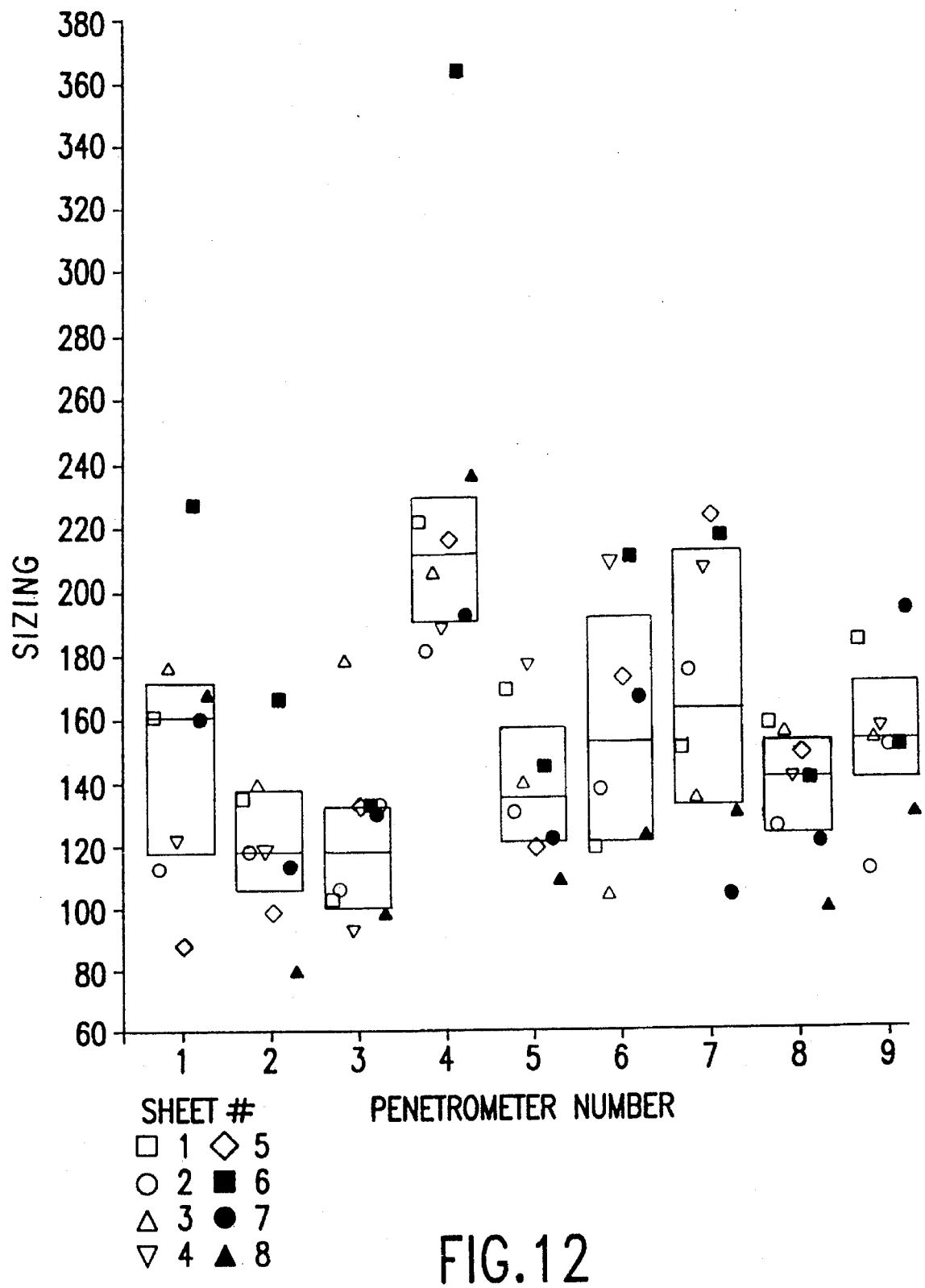

The data generated for the eight sheets of low sized paper appears in Table 1, while the data for the eight sheets of high sized paper appears in Table 2. In both Tables, penetrometer numbers 1–5 correspond to the conventional penetrometers, while numbers 6–9 correspond to penetrometers based on the present invention. The mean sizing value for the eight sheets of low sizing paper and the inter quartile range (IRQ) which represents the distribution range for each of the eight sizing values measured by a given penetrometer appear in Table 3. The mean sizing value for the eight sheets of high sizing paper and the inter quartile range (IQR), which represents the distribution range for each of the eight sizing values measured by a given penetrometer, appear in Table 4. FIGS. 11 and 12 are plots of the data in Tables 3 and 4, respectively.

TABLE 1

| SHEET NUMBER | INK PENETOMETER | SIZING[1] VALUE |
|---|---|---|
| 1 | 1 | 73 |
| 1 | 2 | 49 |
| 1 | 3 | 54 |
| 1 | 4 | 69 |
| 1 | 5 | 45 |
| 1 | 6 | 78 |
| 1 | 7 | 58 |
| 1 | 8 | 71 |
| 1 | 9 | 49 |
| 2 | 2 | 53 |
| 2 | 3 | 56 |
| 2 | 4 | 120 |
| 2 | 5 | 83 |
| 2 | 6 | 58 |
| 2 | 7 | 63 |
| 2 | 8 | 62 |
| 2 | 9 | 63 |
| 3 | 1 | 50 |
| 3 | 2 | 54 |
| 3 | 3 | 67 |
| 3 | 4 | 84 |
| 3 | 5 | 60 |
| 3 | 6 | 57 |
| 3 | 7 | 57 |
| 3 | 8 | 57 |
| 3 | 9 | 65 |
| 4 | 1 | 51 |
| 4 | 2 | 55 |
| 4 | 3 | 61 |
| 4 | 4 | 117 |
| 4 | 5 | 61 |
| 4 | 6 | 67 |
| 4 | 7 | 61 |
| 4 | 8 | 83 |
| 4 | 9 | 38 |
| 5 | 1 | 75 |
| 5 | 2 | 46 |
| 5 | 3 | 57 |
| 5 | 4 | 97 |
| 5 | 5 | 78 |
| 5 | 6 | 82 |
| 5 | 7 | 83 |
| 5 | 8 | 21 |

TABLE 1-continued

| SHEET NUMBER | INK PENETOMETER | SIZING[1] VALUE |
|---|---|---|
| 5 | 9 | 84 |
| 6 | 1 | 73 |
| 6 | 2 | 66 |
| 6 | 3 | 35 |
| 6 | 4 | 90 |
| 6 | 5 | 78 |
| 6 | 6 | 80 |
| 6 | 7 | 86 |
| 6 | 8 | 80 |
| 6 | 9 | 89 |
| 7 | 1 | 62 |
| 7 | 2 | 39 |
| 7 | 3 | 43 |
| 7 | 4 | 58 |
| 7 | 5 | 54 |
| 7 | 6 | 73 |
| 7 | 7 | 62 |
| 7 | 8 | 67 |
| 7 | 9 | 82 |
| 8 | 1 | 58 |
| 8 | 2 | 69 |
| 8 | 3 | 61 |
| 8 | 4 | 71 |
| 8 | 5 | 59 |
| 8 | 6 | 59 |
| 8 | 7 | 54 |
| 8 | 8 | 68 |
| 8 | 9 | 79 |

[1] in seconds

TABLE 2

| SHEET NUMBER | INK PENETOMETER | SIZING[1] VALUE |
|---|---|---|
| 1 | 1 | 160 |
| 1 | 2 | 134 |
| 1 | 3 | 101 |
| 1 | 4 | 221 |
| 1 | 5 | 168 |
| 1 | 6 | 118 |
| 1 | 7 | 149 |
| 1 | 8 | 157 |
| 1 | 9 | 183 |
| 2 | 1 | 112 |
| 2 | 2 | 117 |
| 2 | 3 | 105 |
| 2 | 4 | 180 |
| 2 | 5 | 129 |
| 2 | 6 | 136 |
| 2 | 7 | 173 |
| 2 | 8 | 123 |
| 2 | 9 | 110 |
| 3 | 1 | 175 |
| 3 | 2 | 138 |
| 3 | 3 | 177 |
| 3 | 4 | 205 |
| 3 | 5 | 138 |
| 3 | 6 | 103 |
| 3 | 7 | 133 |
| 3 | 8 | 154 |
| 3 | 9 | 152 |
| 4 | 1 | 121 |
| 4 | 2 | 118 |
| 4 | 3 | 92 |
| 4 | 4 | 187 |
| 4 | 5 | 176 |
| 4 | 6 | 209 |
| 4 | 7 | 205 |
| 4 | 8 | 140 |
| 4 | 9 | 156 |
| 5 | 1 | 88 |
| 5 | 2 | 98 |
| 5 | 3 | 131 |

TABLE 2-continued

| SHEET NUMBER | INK PENETOMETER | SIZING[1] VALUE |
|---|---|---|
| 5 | 4 | 215 |
| 5 | 5 | 118 |
| 5 | 6 | 171 |
| 5 | 7 | 222 |
| 5 | 8 | 147 |
| 5 | 9 | 150 |
| 6 | 1 | 227 |
| 6 | 2 | 165 |
| 6 | 3 | 131 |
| 6 | 4 | 365 |
| 6 | 5 | 143 |
| 6 | 6 | 210 |
| 6 | 7 | 216 |
| 6 | 8 | 139 |
| 6 | 9 | 150 |
| 7 | 1 | 159 |
| 7 | 2 | 112 |
| 7 | 3 | 129 |
| 7 | 4 | 191 |
| 7 | 5 | 120 |
| 7 | 6 | 73 |
| 7 | 7 | 62 |
| 7 | 8 | 67 |
| 7 | 9 | 82 |
| 8 | 1 | 58 |
| 8 | 2 | 69 |
| 8 | 3 | 61 |
| 8 | 4 | 71 |
| 8 | 5 | 59 |
| 8 | 6 | 59 |
| 8 | 7 | 54 |
| 8 | 8 | 68 |
| 8 | 9 | 79 |

[1] in seconds

TABLE 3

| INK PENETOMETER NUMBER | MEAN SIZING VALUE OF THE 8 PAPER SHEETS (LOW SIZING) | INTER QUARTILE RANGE |
|---|---|---|
| 1 | 63 | 18 |
| 2 | 54 | 13 |
| 3 | 54 | 12 |
| 4 | 88 | 37 |
| 5 | 65 | 22 |
| 6 | 69 | 20 |
| 7 | 66 | 16 |
| 8 | 64 | 16 |
| 9 | 68 | 27 |

TABLE 4

| INK PENETOMETER NUMBER | MEAN SIZING VALUE OF THE PAPERSHEETS (HIGH SIZING) | INTER QUARTILE RANGE |
|---|---|---|
| 1 | 151 | 54 |
| 2 | 120 | 31 |
| 3 | 120 | 32 |
| 4 | 225 | 40 |
| 5 | 138 | 36 |
| 6 | 154 | 71 |
| 7 | 166 | 80 |
| 8 | 135 | 30 |
| 9 | 153 | 30 |

The above-described preferred embodiment is but one example of an improved penetrometer constructed in accordance with the present invention. A variety of alternative embodiments are possible. For example, the entire electronics could be implemented using fully synchronous digital circuitry. In that case, sample & hold amplifier 40 would be an analog-to-digital converter and register, voltage comparator 50 would be a digital comparator, and the various timers would be replaced by synchronous counters, all operating off a central clock. Of course, a microprocessor might also be used to control the operation of the penetrometer. It is therefore the inventors' intent that the scope of this invention be defined only by the claims that appear below, and that the means-plus-function elements in these claims be construed broadly to cover both the analog circuitry (and equivalents thereof) employed in the preferred embodiment, as well as suitable digital circuitry capable of performing the same (or an equivalent) function.

What is claimed is:

1. A penetrometer for measuring the rate of penetration of a fluid through a sample, said penetrometer comprising:
   means for applying fluid to a first surface of said sample;
   means for optically detecting the penetration of said fluid to, or proximate to, a second surface of said sample; and
   timing means, coupled to said means for applying and said means for optically detecting, for measuring the time between the application of said fluid to said first surface and the optical detection of said fluid on, or proximate to, said second surface;
   wherein said means for applying fluid remains in a fixed position with respect to said sample.

2. A penetrometer as defined in claim 1 wherein said means for applying fluid comprises a fixed paddle having a fluid well.

3. A penetrometer as defined in claim 2 wherein said means for applying fluid further comprises a fill port for providing fluid to said well.

4. A penetrometer as defined in claim 2 wherein said means for applying fluid further comprises a drain port for removing fluid from said well.

5. A penetrometer for measuring the rate of penetration of a fluid through a sample, said penetrometer comprising:
   means for applying fluid to a first surface of said sample;
   means for optically detecting the penetration of said fluid to, or proximate to, a second surface of said sample comprising:
      means for illuminating said second surface comprising a light source and a first fiber optic cable; and
      means for detecting light reflected from said second surface comprising a second fiber optic cable and a photodetector; and
   timing means, coupled to said means for applying and said means for optically detecting, for measuring the time between the application of said fluid to said first surface and the detection of a diminished level of light reflected from said second surface indicating that said fluid is on or proximate to said second surface.

6. A penetrometer as defined in claim 5 wherein said source and said photodetector are physically separated.

7. A penetrometer as defined in claim 5 wherein said photodetector is isolated from the fluid.

8. A penetrometer as defined claim 5, wherein said first fiber optic cable couples light from said light source to a photohead.

9. A penetrometer as defined in claim 5, wherein said second fiber optic cable couples said reflected light from a photohead to said photodetector.

10. A penetrometer as defined in claim 6, further comprising means for automatically locking in an initial reflectance value at the start of each test cycle.

11. A penetrometer as defined in claim 8, further comprising means for holding said photohead proximate to said means for applying ink and for holding said sample in between.

12. A penetrometer as defined in claim 5 wherein said means for detecting light reflected from said second surface further comprises a built-in amplifier.

13. A penetrometer as defined in claim 5, further comprising means for automatically storing, at the start of each test, an initial reflectance value indicative of the light reflected from the second side of said sample before any fluid has been applied to said sample.

14. A penetrometer as defined in claim 13, further comprising means for generating a threshold signal indicative of a predetermined percentage of said initial reflectance value.

15. A penetrometer as defined in claim 14, further comprising means for comparing said threshold signal to a signal indicative of the light currently reflected off the second side of said sample.

16. A penetrometer as defined in claim 15, further comprising a counter for counting the time from the application of ink to the first surface of said sample to the time at which the light reflected off the second surface of said sample drops below the value of said threshold signal.

17. A penetrometer as defined in claim 13, further comprising means for continuously displaying a value indicative of the ratio of the light reflected off the second surface of said sample to the value of said threshold signal.

18. A penetrometer as defined in claim 5, wherein said first and second fiber optic cables merge to form a bifurcated fiber optic cable.

19. A penetrometer as defined in claim 5, wherein said means for applying fluid is adapted to remain in a fixed position during operation of the penetrometer.

20. A penetrometer as defined in claim 5 wherein said timing means comprises a microprocessor.

* * * * *